(12) United States Patent
Mosca et al.

(10) Patent No.: US 6,797,269 B2
(45) Date of Patent: Sep. 28, 2004

(54) MESENCHYMAL STEM CELLS AS IMMUNOSUPPRESSANTS

(75) Inventors: Joseph D. Mosca, Ellicott City, MD (US); Kevin R. McIntosh, Ellicott City, MD (US)

(73) Assignee: Osiris Therapeutics, Inc., Baltimore, MD (US)

( * ) Notice: Subject to any disclaimer, the term of this patent is extended or adjusted under 35 U.S.C. 154(b) by 0 days.

(21) Appl. No.: 09/267,456

(22) Filed: Mar. 12, 1999

(65) Prior Publication Data

US 2002/0044923 A1 Apr. 18, 2002

Related U.S. Application Data

(60) Provisional application No. 60/080,678, filed on Apr. 3, 1998.

(51) Int. Cl.$^7$ .................................................. A61K 39/00
(52) U.S. Cl. ................................ 424/184.1; 424/93.21; 424/93.7; 424/192.1; 435/346; 435/366; 435/372
(58) Field of Search ............................. 424/93.21, 93.7; 435/346, 366, 372, 184.1, 192.1

(56) References Cited

U.S. PATENT DOCUMENTS 5,591,625 A * 1/1997 Gerson et al.
5,747,299 A * 5/1998 Bloom et al.
5,962,320 A * 10/1999 Robinson

OTHER PUBLICATIONS

Janeucy et al. Immunobiology pp. 4:1–4:9, 1994.*
Paul, ed. Fundamental Immunology pp. 265–268 and 1183, 1999.*
Brenner, Michael and Porcelli, Steven, "Antigen Presentation: A Balanced Diet," *Science*, 277:332 (*1997*).

* cited by examiner

*Primary Examiner*—G. R. Ewoldt
(74) *Attorney, Agent, or Firm*—Elliot M. Olstein; Raymond J. Lillie

(57) ABSTRACT

The present invention provides a method to modulate immune responses using antigen presenting human mesenchymal stem cells to induce specific T cell anergy. The present invention also provides a method to modulate immune responses using human mesenchymal stem cells as a platform to express molecules which will induce T cell anergy.

16 Claims, 4 Drawing Sheets membrane-bound CTLA-4 soluble-form CTLA4-Ig

MESENCHYMAL STEM CELLS AS IMMUNOSUPPRESSANTS

This application is based on and claims priority of U.S. provisional application Ser. No. 60/080,678 filed Apr. 3, 1998.

The present invention relates to the field of inducing immunosuppression by using mesenchymal stem cells to inhibit T cell activation against antigens.

BACKGROUND OF THE INVENTION

In a normal immune response, T cells are activated by a first, antigen specific, signal which stimulates T cells via the T cell antigen receptor and confers antigen specificity to the immune response; and a second, costimulatory, signal delivered by costimulatory molecules found on the surface of antigen presenting cells. Both signals are required to induce T cell proliferation. If the second costimulatory signal does not occur, or if the co-stimulation pathway is blocked or downregulated, activation of T cells will be reduced or eliminated. This results in hyporesponsiveness of the T cells to antigen and can induce a state of T cell anergy, or T cell nonresponsiveness, wherein the T cells will not proliferate when presented with antigen.

The best characterized co-stimulatory molecules on antigen-presenting cells are the structurally related glycoproteins B7-1 (CD80) and B7-2 (CD86). These are homodimeric members of the immunoglobulin superfamily found exclusively on the surface of cells capable of stimulating T-cell growth. The receptor for B7 molecules on the T-cell is CD28, another member of the immunoglobulin superfamily. Ligation of CD28 by B7-1 or B7-2 or by anti-CD28 antibodies will co-stimulate the growth of naive T-cells, while antibodies to the B7 molecules, which inhibit B7 binding to CD28, inhibit T-cell responses.

The function of the immune system is to eliminate foreign cells that may contain pathogens, while maintaining unresponsiveness or tolerance against self-antigens. Tolerance is manifested by T cell anergy, characterized by the survival, but nonresponsiveness of T cells. However, the immune system may attack self-constituents, causing autoimmune disease. Autoimmune diseases are believed to originate in the abnormal immune response to self-antigens, either due to a change in self-antigens or exposure to crossreactive antigens. Autoimmune diseases caused by antibody-mediated immune responses to self-antigens include diseases such as rheumatoid arthritis, systemic lupus erythematosus and inflammatory bowel disease.

It is desirable to improve present treatments of autoimmune disease or other undesirable immune reactions which use general immunosuppressive agents such as corticosteroids, azathioprine, or cyclosporine A. These treatments are nonselective and do not distinguish between normal and abnormal immune responses. These drugs often have adverse side effects, including general suppression of the immune system with risks of infection and neoplasia, as well as the development of diseases such as diabetes, osteoporosis, leukopenia and hypertension.

Accordingly, in certain circumstances, such as autoimmune disease, a particular immune response may not be desired. Alternative approaches for treatment of these conditions are needed for patients who cannot withstand, or do not respond to, conventional chronic, non-specific drug therapy.

SUMMARY OF THE INVENTION

It has been discovered that human mesenchymal stem cells can be used to deliver antigens to the immune system such that an immune response to the antigen will be inhibited, i.e. eliminated, reduced or ameliorated. The reduction or elimination of an immune response by mesenchymal stem cells as described herein can be used as a method to ameliorate an immune response in a recipient against autoimmune disease.

Accordingly the methods of the present invention are particularly useful for eliminating, reducing or ameliorating unwanted or abnormal T cell immune responses. In one aspect the method involves administering to an animal mesenchymal stem cells which have been modified to carry an antigen. Presentation of the antigen to the T cell in the absence of a costimulatory signal induces an antigen-specific state of hyporesponsiveness, or even nonresponsiveness or anergy in the T cell to subsequent challenge to the T cell by the antigen. Thus, an immune response is reduced or eliminated. The elimination, reduction or amelioration of an immune response as described herein can be used as a method to treat or inhibit an unwanted or abnormal immune response such as occurs in autoimmune disease.

In another aspect of the present invention mesenchymal stem cells can be used to present to the immune system molecules that block costimulation pathways which are required to effect an immune response. The elimination, reduction or amelioration of an immune response as described herein can be used as a method to treat or inhibit an unwanted or abnormal immune response such as occurs in autoimmune disease. Blocking the costimulatory signal inhibits T cell activation by antigen specific signals presented by antigen presenting cells that may be in the proximity of the T cells.

In a still further aspect of the invention, the mesenchymal stem cells are used to deliver to the T cells an antigen and a molecule that inhibits the delivery of a costimulation signal to the T cells. Delivering a specific antigen to target T cells in conjunction with blocking the costimulatory signal inhibits specific T cell activation in the presence of antigen specific signal presented by the antigen-presenting mesenchymal stem cell. In a preferred embodiment, molecules that block T cell costimulation are selected from cytotoxic T-lymphocyte-associated protein 4 (CTLA-4) or CTLA-4Ig, a fusion protein of CTLA-4 and the constant region of human IgG-1.

DETAILED DESCRIPTION OF PREFERRED EMBODIMENTS

Figure 1:
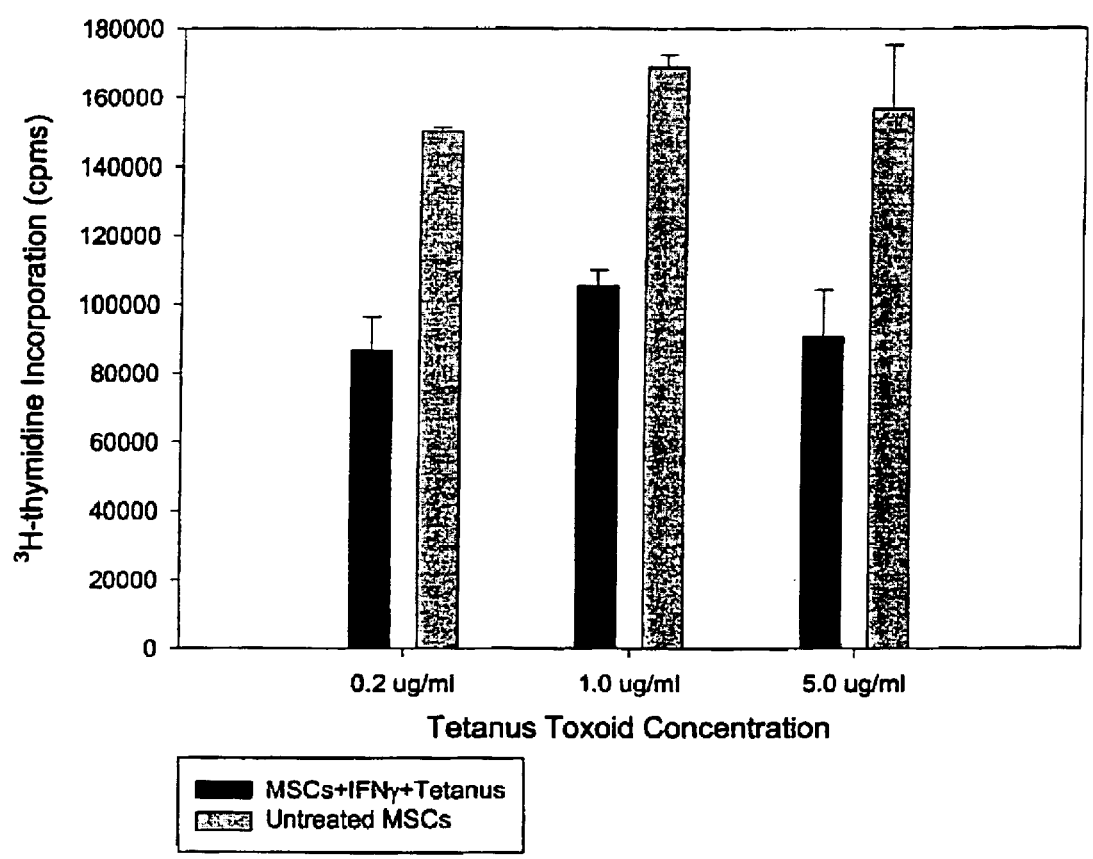
FIG. 1 shows a reduction in the proliferative response of tetanus toxoid specific T cells to restimulation using peripheral blood mononuclear cells as antigen presenting cells after the T-cells were co-cultured with mesenchymal stem cells that were pulsed with tetanus toxoid.

This invention relates to methods for reducing, inhibiting or ameliorating an immune response to a specific antigen, in vivo, by employing mesenchymal stem cells as antigen presenting cells to present antigen to the animal. The mesenchymal stem cells ameliorate, inhibit or reduce the T cell response to the antigen because the mesenchymal stem cells do not produce, or do not produce sufficient amounts of, the costimulatory signal required to activate the T cells. Instead, the mesenchymal stem cells induce hyporesponsiveness of a targeted T cell population to antigen, i.e., there is an ameliorated, inhibited or reduced T cell immune response to the antigen upon subsequent presentation of the antigen to the T cell.

Accordingly, the mesenchymal stem cells can be modified to present antigen to a target T cell population comprising T cells having receptors for the specific antigen. In one embodiment, the mesenchymal stem cells are modified by contact with antigen in vitro. In another embodiment, the mesenchymal stem cells are genetically manipulated to express an antigenic molecule. The mesenchymal cells are preferably autologous to the recipient of the mesenchymal stem cells.

As used herein, the term antigen is intended to include a protein, polypeptide, lipid, glycoprotein, etc. In one aspect of the invention, mesenchymal stem cells are modified to have at least one exogenous antigen fragment bound to a primary surface molecule of the cell such that at least one antigen fragment is presented to inhibit or reduce the proliferative response of lymphocytes. In one embodiment, the mesenchymal stem cell is contacted with at least one antigen (antigen-pulsing). The mesenchymal stem cell processes the antigen into an antigen fragment for presentation by the mesenchymal stem cells. In another embodiment, the mesenchymal stem cell is genetically manipulated to express an antigenic molecule.

In another aspect of the invention, it is contemplated that the mesenchymal stem cells are modified to express a specific autoantigen, particularly an autoantigen that mediates the immune response in autoimmune diseases.

The present invention further relates to a method of inhibiting, ameliorating or reducing a T cell response to a specific antigen by administering, in vivo, mesenchymal stem cells used as antigen presenting cells, with the mesenchymal stem cells being further modified with a molecule that blocks the delivery of a T cell costimulation signal to the targeted T cell. The target T cell population may or may not have already been presented once with antigen. Thus, in addition to inducing hyporesponsiveness of the T cells to challenge by the antigen, the mesenchymal stem cells further ameliorate, inhibit or reduce the T cell immune response by blocking costimulatory signals to the T cell that may be provided by an antigen presenting cell. This treatment inhibits full activation of the T cells and results in hyporesponsiveness or even nonresponsiveness of the T cells.

With respect to this aspect of the invention, the antigen presenting cells that provide costimulatory signals to the T cells can be endogenous antigen presenting cells or may be the antigen-presenting mesenchymal stem cell. In the case where mesenchymal stem cells which may express the costimulatory signal required to activate T cells are used, these mesenchymal stem cells will be further modified with a molecule that blocks delivery of the costimulatory signal.

In accordance with this aspect of the invention, it is contemplated that the mesenchymal stem cells are modified to express a specific autoantigen, particularly an autoantigen that mediates the immune response in autoimmune diseases.

According to the method of the present invention, a molecule that inhibits the delivery of a costimulatory signal to a T cell is one that interferes with the T cell costimulation pathway such that the T cells do not proliferate against antigen as occurs in a normal immune response. As the term is used herein, a T cell costimulation signal is delivered when a costimulatory molecule interacts with its T cell receptor. Accordingly, in a preferred embodiment, the method involves the expression of a molecule by the mesenchymal stem cells which will block or interfere with such interaction. By blocking this interaction on primed T cells (i.e., T cells already presented with the first antigen specific signal), full activation of the T cells by antigen presenting cells is inhibited. The T cells exhibit hyporesponsiveness or nonresponsiveness to antigen, which results in an amelioration, reduction or elimination of an immune response by the T cells against antigen.

In a preferred embodiment of this aspect of the invention, the costimulatory molecules are B7-1 and B7-2 and the T cell receptor is CD28. In accordance with this embodiment, the mesenchymal stem cell is preferably genetically engineered to express CTLA-4 or CTLA4-Ig. Both CTLA-4 and CTLA4-Ig interfere with the interaction of B7 and CD28, thus inhibiting the delivery of the costimulatory signal by the antigen to the T cell.

Activated T-cells express the receptor CTLA-4, in addition to CD28, which binds B7 molecules with a higher affinity than does CD28. CTLA-4 closely resembles CD28 in sequence, and the two molecules are encoded by closely linked genes. CTLA-4 is a competitive antagonist of CD 28. CTLA-4 inhibits the delivery of costimulatory signal, by either outcompeting CD28 for binding to B7 or downregulating the signal, resulting in the inhibition of full activation, and therefore proliferation of the T-cell expressing it.

A soluble form of CTLA-4 is the fusion protein CTLA4-Ig. The CTLA-4 molecule is incorporated as part of a fusion protein that contains a region that increases the stability and solubility of the molecule. Blocking of T cell activation by CTLA4-Ig, the B7 specific fusion protein, has also been described (Kirk, et. al., PNAS 1997).

In a still further aspect, the method of the present invention reduces, inhibits or ameliorates an immune response to an antigen, in vivo, by employing mesenchymal stem cells as a vehicle to present to the immune system a molecule that blocks T cell costimulation. The mesenchymal stem cells induce hyporesponsiveness or nonresponsiveness of the T cell to an antigen by interference with the delivery of a costimulatory signal to the T cell. This results in a reduction, amelioration or elimination of the T cell immune response to an antigen after presentation of the antigen to the T cell.

Accordingly, the mesenchymal stem cells can be modified to present to the immune system a molecule that blocks or interferes with delivery of a costimulatory signal to a T cell that may already be primed with an antigen specific signal from an endogenous antigen presenting cell. The mesenchymal stem cells are preferably modified to express CTLA-4 or CTLA4-Ig. In one embodiment, the mesenchymal stem cells are genetically manipulated to express the blocking molecules prior to contact with the T cells. The molecule may be membrane-bound or it may be a soluble protein. In accordance with this aspect, after the mesenchymal stem cells are administered, the method results in blocking of costimulation of T cells by antigen presenting cells and, thus, a subsequent reduced T cell immune response is obtained.

In a preferred embodiment of this aspect of the invention, mesenchymal stem cells are used as a platform to express cytotoxic T-lymphocyte-associated protein 4 (CTLA-4) or CTLA-4Ig, a fusion protein of CTLA-4 and the constant region of human IgG1, molecules that block T cell costimulation.

In accordance with this aspect of the invention, the amelioration, reduction or elimination of a nonspecific immune response is enabled. The application of the method is not limited to a particular antigen-specific T cell population, but can be applied to any antigen specific T cell mediated immune response to ameliorate, reduce or eliminate the immune response. In this embodiment the mesenchymal stem cells are preferably administered locally. The mesenchymal stem cells can be either allogeneic to or autologous to the individual to whom they are being administered, preferably autologous.

Mesenchymal stem cells are normally present in minute amounts in bone marrow, however a process has been developed for isolating, purifying, and greatly replicating these cells in culture, i.e. in vitro. See, Caplan and Haynesworth, U.S. Pat. No. 5,486,359.

The human mesenchymal stem cells can be used as hosts for foreign genes for the expression of gene products in systemic or localized targets. The human mesenchymal stem cells of the invention can be engineered (transduced or transformed or transfected) with genetic material of interest. The engineered human mesenchymal stem cells can be cultured in conventional nutrient media modified as appropriate for activating promoters, selecting transformants or amplifying exogenous genes therein. The culture conditions, such as temperature, pH and the like, can be those previously used with engineered human mesenchymal stem cells. See, for example, Gerson et al., U.S. Pat. No. 5,591,625. Mesenchymal stem cells can be treated with IFN-gamma to stimulate MHC presentation by the mesenchymal stem cells.

Unless otherwise stated, genetic manipulations are performed as described in Sambrook and Maniatis, Molecular Cloning: A Laboratory Manual, Cold Spring Harbor Laboratory, 1989.

Although not limited to the treatment of autoimmune disease, the mesenchymal stem cells and method of the invention can accordingly be appropriately applied to treatment strategies requiring immunosuppressive reagents. Also contemplated is the modification of and expansion of mesenchymal stem cells in vitro for use in cellular immunotherapy, the in vivo administration of the immunosuppressive mesenchymal stem cells for treating or preventing unwanted immune responses. One aspect of the invention is the development of the mesenchymal stem cells into a vehicle for delivering inhibitory signals or antigen to target a specific cellular response, the development of vaccines with the mesenchymal stem cells modified as described herein for either target specific or systemic delivery of immunosuppression for prophylaxis and therapy of disease.

Typically, in the prophylaxis or treatment of disease states, the recipient is most preferably only required to undergo a single administration after which disease remission is realized on a permanent basis. Alternatively, depending upon observation of follow-up monitoring, any subsequent administration may be of greater or lesser doses. Such procedures and monitoring regimens are well known to those who are versed in the field of immune therapy, infectious disease, oncology, epidemiology and the like.

The dosage of the active ingredient varies within wide limits and will, of course be fitted to the individual requirements in each particular case. In general, in the case of parenteral administration, it is customary to administer from about 0.5 to about 5 million cells per kilogram of recipient body weight. The number of cells used will depend on the weight and condition of the recipient and other variables known to those of skill in the art. The cells can be administered by a route which is suitable for the particular disease state to be treated. In the case of non-specific induction of hyporesponsiveness of the immune response, mesenchymal stem cells modified with CTLA-4, for example, can be administered systemically, i.e. parenterally, intravenously or by injection. In the case of induction of antigen specific hyporesponsiveness, the antigen-modified mesenchymal stem cells can be targeted to a particular tissue or organ, such as bone marrow.

The cells can be suspended in an appropriate diluent, at a concentration of from about $5 \times 10^6$ to about $50 \times 10^6$ cells/ml. Suitable excipients for injection solutions are those that are biologically and physiologically compatible with the recipient, such as buffered saline solution. The composition for administration should be sterile, stable, and the like, as is appropriate for administration into an individual.

An advantage of the methods of the present invention over current treatment for unwanted immune responses is specificity; mesenchymal stem cells are targeted to reduce a specific immune response without adversely affecting other segments of the immune system. The amelioration, reduction or elimination of an antigen specific immune response enables the treatment of or prevention of an unwanted or abnormal immune response to a specific antigen. A further advantage is that the mesenchymal stem cells offer localized expression of a molecule of interest. Localized expression of a molecule for example which blocks co-stimulation, e.g. CTLA4-Ig, may result in reduced inflammation and fewer side effects. Examples of diseases which would be particularly suited to treatment with the mesenchymal stem cells of the present invention include thyroiditis, rheumatoid arthritis and insulin dependent diabetes mellitus. The mesenchymal stem cells can further provide a continuous supply of the molecule of interest.

The methods of the present invention are particularly applicable to therapy of autoimmune disease and should preferably inactivate or eliminate the response to autoantigen specifically, without compromising other aspects of the immune system.

The invention can be utilized for treatment of autoimmune diseases where the autoantigen mediating the disease is known. The method involves genetically engineering mesenchymal stem cells, preferably isolated from a patient's own bone marrow, to express an autoantigen in order to induce specific immunotherapy to inactivate or eliminate abnormal immune responses, without interfering with other functions of the immune system.

The following examples further illustrate aspects of the present invention. However, they are in no way a limitation of the teachings or disclosure of the present invention as set forth herein.

EXAMPLES

Materials

CTLA-4 and CTLA-4Ig were expressed in the human mesenchymal stem cells transduced with the cDNA CTLA-4 sequence obtained from Gene Bank Accession # L15006. The Ig form was constructed by fusing the extracellular portion of CTLA-4 with the Fc heavy chain portion of human IgG via a flexible hinge of 4 glycines and 2 serines. Peripheral blood mononuclear cells ("PBMCs") were obtained by apheresis of the same donors of the human mesenchymal stem cells. Commercially available CTLA4-Ig was obtained from R&D Systems (Minneapolis, Minn.). Mouse Ly6A.2 was obtained from Dr. Ethan Shevach and cloned into a MuLVRetroviral Vector.

Tetanus toxoid specific T cell lines were prepared by stimulating PBMCs with 1 µg/ml tetanus toxoid (Connaught Laboratories, Toronto, Canada) for 6 days. The cells were harvested, washed and recultured for an additional 7 days in 20 units/ml recombinant human IL2 (Proleukin) to expand tetanus toxoid specific T cells. The cells were harvested and T cells were purified by removal of B cells and monocytes using magnetic separation. The tetanus toxoid T cell line was aliquoted and frozen in liquid nitrogen until further use.

Example 1

Induction of T Cell Hyporesponsiveness to Tetanus Toxoid Using Mesenchymal Stem Cells MSCs from Donor 155 were plated in 4 T185$^2$ flasks and one flask was treated with 100 U/ml IFN-gamma. After four days the MSCs were harvested (both IFN gamma treated and untreated). $3\times10^5$ MSCs were plated in each well of a 6 well tissue culture plate-1 well with IFN-gamma treated MSCs, 1 well with untreated MSCs. IFN-gamma treated MSCs were pulsed with 50 ug/ml Tetanus toxoid overnight. All wells were washed very thoroughly with 1X Hanks Buffered Salt Solution and $5\times10^6$ Tetanus toxoid specific autologous T cells (Tet T cells) (Donor 155) were added per well. The cultures were incubated for 5 days. The harvested T cells were restimulated with Tetanus toxoid (0, 0.2, 1.0 and 5.0 $\mu$/ml)-PBMCs ($5\times10^5$/well) were used as APCs and the proliferation assay was incubated for 3 days. The cells were then pulsed with 1 uCi [$^3$H]thymidine overnight and the assay was harvested 18 hours later.

The results illustrated in FIG. 1 (control 0 $\mu$g/ml counts subtracted as background) show a decrease (of approximately 30–40%) in the proliferative response or restimulation potential of the Tet T cells after 5 days co-culture with the IFN-gamma/Tetanus toxoid treated MSCs compared to the proliferative response of the Tet T cells co-cultured with untreated MSCs.

Example 2

Figure 2A:
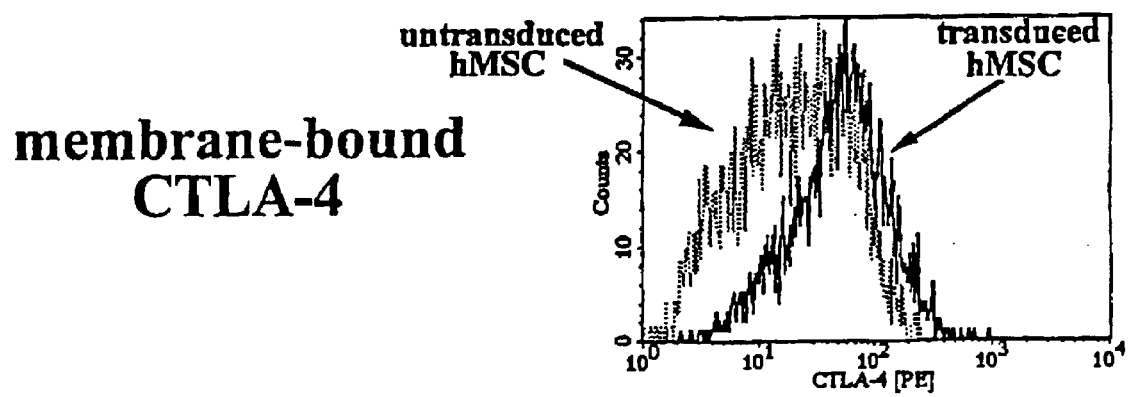
FIG. 2. Flow cytometry analyses of human mesenchymal stem cells confirming the transduction of the cells with CTLA-4 (membrane bound) (FIG. 2A) and soluble form CTLA4-Ig (FIG. 2B).

Blocking of T cell Activation by Tetanus Toxoid with CTLA-4 (Membrane-bound) Transduced Mesenchymal Stem Cells Human mesenchymal stem cells were transduced with either the full-length human CTLA-4 gene or with a mouse surface molecule (mouse Ly6A.2) as a control. FIG. 2A shows the Flow Cytometry Analysis of the human mesenchymal stem cells transduced with CTLA-4. The control and the CTLA-4 transduced human mesenchymal stem cells were treated with IFN-gamma for three days to elevate MHC class II expression and were pulsed with high-dose (100 ug/ml) tetanus toxoid for one day. After removal of IFN-gamma and tetanus toxoid from the cultures, a tetanus toxoid specific T cell line (TetC) was added to the human mesenchymal stem cells and the cultures were incubated for 3 days. Lymphoproliferation of the T cell line was assessed by uptake of [$^3$H]thymidine during the final 8 hours of the culture period.

Figure 3:
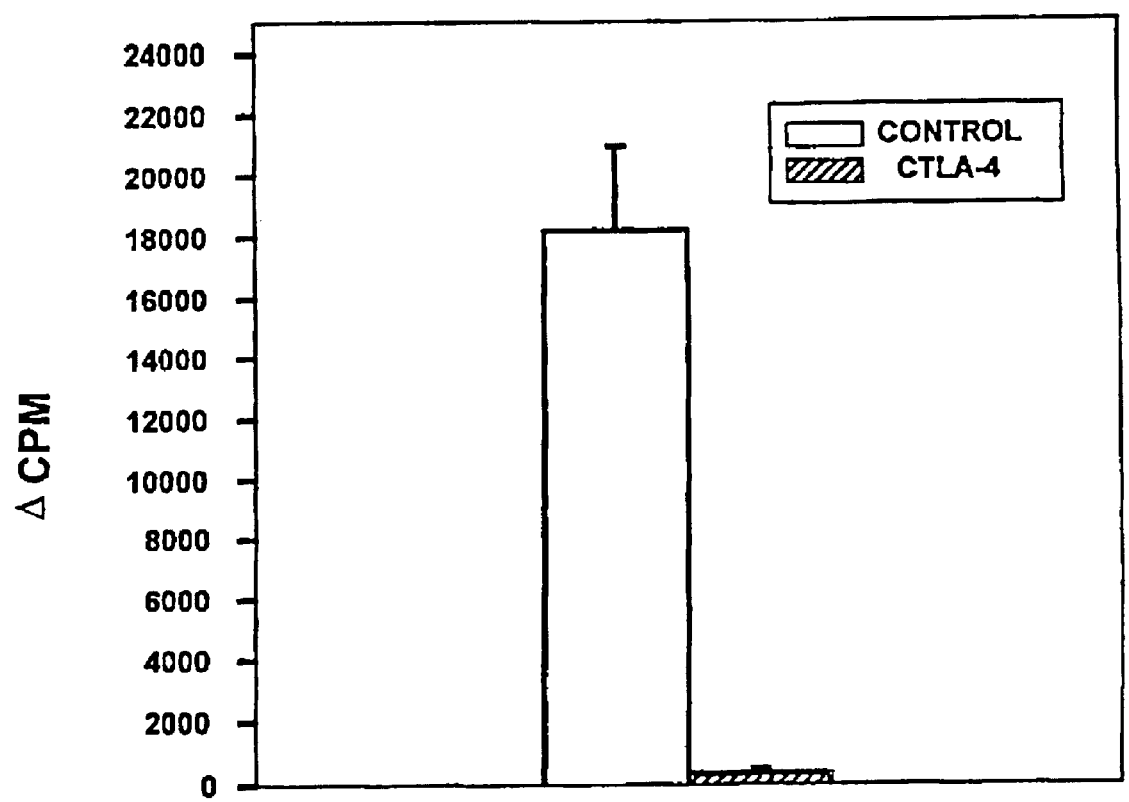
FIG. 3. Inhibition of T cell stimulation by human mesenchymal stem cells transduced with CTLA-4.

The results, shown in FIG. 3, indicated that the control transduced human mesenchymal stem cells presented tetanus toxoid to the T cells present in the PBMC preparation, and resulted in T cell proliferation (18,000 cpms), whereas the CTLA-4 transduced human mesenchymal stem cells did not induce a T cell response (200 cpms). These results demonstrated that the expression of the CTLA-4 molecule on the human mesenchymal stem cells suppressed the T cell response.

Example 3

Figure 2B:
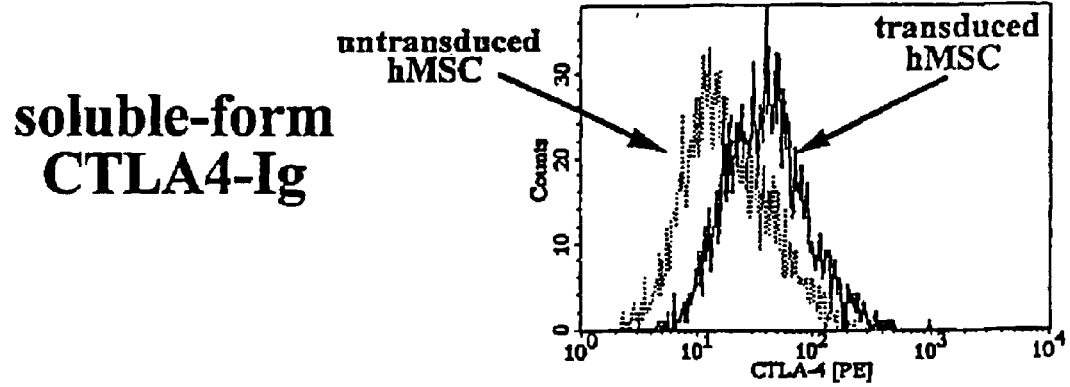
Figure 4:
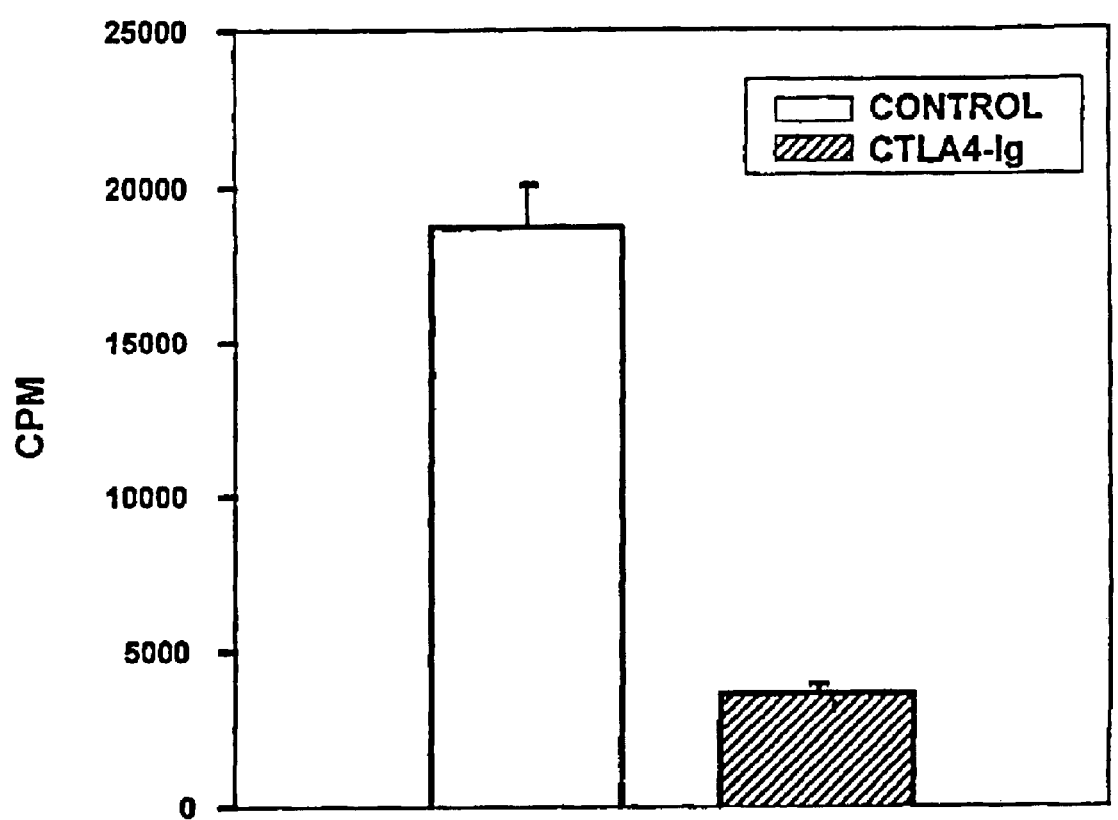
FIG. 4. Inhibition of T cell stimulation by human mesenchymal stem cells transduced with CTLA4-Ig.

Blocking of T cell Activation by Tetanus Toxoid with CTLA4-Ig (Soluble-form) Transduced Mesenchymal Stem Cells Human mesenchymal stem cells were transduced with either the soluble form CTLA4-Ig, which is composed of the extracellular portion of the human CTLA-4 gene fused to the constant region of human IgG1, or with a mouse surface molecule (mouse Ly6A.2) as a control. FIG. 2B shows the Flow Cytometry Analysis of the mesenchymal stem cells transduced with CTLA4-Ig. To sub-confluent cultures of the control and CTLA4-Ig transduced human mesenchymal stem cells, tetanus toxoid antigen (1 ug/ml) and peripheral blood mononuclear cells (PBMCs) (100,000 cells/well) were added. Lymphoproliferation of the T cells present within the PBMC preparation was assessed by uptake of [$^3$H]thymidine during the final 8 hours of the culture period (FIG. 4). Additional controls were performed where PBMCs were exposed to antigen in the presence of commercially available CTLA4-Ig protein in the absence of human mesenchymal stem cells. The results show that the CTLA4-Ig transduced human mesenchymal stem cells provided an 81% inhibition in lymphoproliferation (4,000 cpms), whereas control transduced human mesenchymal stem cells did not inhibit proliferation of T cells present in the PBMC preparation to tetanus toxoid (19,000 cpms). The inhibition (81%) in lymphoproliferation observed with human mesenchymal stem cells expressing CTLA4-Ig was greater than the level of inhibition observed with the commercially available CTLA4-Ig protein (5 ug/ml) which inhibited PBMC lymphoproliferation by only 51%. Thus, the expression of the CTLA4-Ig molecule on the human mesenchymal stem cells suppressed T cell responses to levels well below those shown for commercially available CTLA4-Ig.

What is claimed is:

1. A method of inhibiting a T-cell response to an antigen, comprising;

culturing mesenchymal stem cells in the presence of IFN-γ;

modifying said mesenchymal stem cells to present said antigen by contacting said mesenchymal stem cells with said antigen in vitro, wherein said mesenchymal stem cells do not produce co-stimulatory molecules in a sufficient amount to activate T-cells, whereby said mesenchymal stem cells present said antigen; and administering to a host said modified mesenchymal stem cells, thereby inhibiting a T-cell response to said antigen upon subsequent exposure of the T-cells to antigen presenting cells which express co-stimulatory molecules.

2. The method of claim 1 wherein said mesenchymal stem cells do not produce co-stimulatory molecules.

3. The method of claim 1 wherein said mesenchymal stem cells are genetically engineered to express a molecule to block co-stimulation of T-cells.

4. The method of claim 3 wherein the molecule is membrane-bound.

5. The method of claim 4 wherein the molecule is CTLA-4.

6. The method of claim 3 wherein the molecule is a soluble protein.

7. The method of claim 6 wherein the molecule is CTLA-4-Ig fusion protein.

8. A method of inhibiting a T-cell response to an antigen, comprising:

culturing mesenchymal stem cells in the presence of IFN-γ;

modifying human mesenchymal stem cells to present said antigen by genetically engineering said human mesenchymal stem cells to express said antigen, wherein said human mesenchymal stem cells do not produce co-stimulatory molecules in a sufficient amount to activate T-cells, whereby said human mesenchymal stem cells present said antigen; and administering to a host said modified human mesenchymal stem cells, thereby inhibiting a T-cell response to said antigen upon subsequent exposure of the T-cells to antigen presenting cells which express co-stimulatory molecules.

9. The method of claim 8 wherein the antigen is an autoantigen.

10. The method of claim 8 wherein the human mesenchymal stem cells are autotogous to the host.

11. The method of claim 8 wherein said mesenchymal stem cells do not produce co-stimulatory molecules.

12. The method of claim 8 wherein said mesenchymal stem cells are genetically engineered to express a molecule to block co-stimulation of T-cells.

13. The method of claim 12 wherein the molecule is membrane-bound.

14. The method of claim 13 wherein the molecule is CTLA-4.

15. The method of claim 12 wherein the molecule is a soluble protein.

16. The method of claim 15 wherein the molecule is CTLA-4-Ig fusion protein.

* * * * *